(12) United States Patent
Hu et al.

(10) Patent No.: US 6,943,024 B2
(45) Date of Patent: Sep. 13, 2005

(54) EPIDERMAL MELANOCYTE CULTURE FORMULATIONS

(76) Inventors: Dan-Ning Hu, 209-54 45th Dr., Bayside, NY (US) 11361; Steven McCormick, 112 E. 19th St., Apt 9F, New York, NY (US) 10003

( * ) Notice: Subject to any disclaimer, the term of this patent is extended or adjusted under 35 U.S.C. 154(b) by 0 days.

(21) Appl. No.: 10/670,971

(22) Filed: Sep. 24, 2003

(65) Prior Publication Data

US 2005/0064588 A1 Mar. 24, 2005

(51) Int. Cl.[7] .............................. C12N 5/00; C12N 5/02; A01N 63/00
(52) U.S. Cl. ....................... 435/406; 435/387; 435/325; 424/93.1
(58) Field of Search .......................... 424/93.2; 435/325, 435/371, 384, 391

(56) References Cited

U.S. PATENT DOCUMENTS 5,916,809 A * 6/1999 Yanase et al. ............... 435/405
5,925,682 A * 7/1999 Gruber et al. ............... 514/653

OTHER PUBLICATIONS

Chen et al. Transplant of cultured autologous pure melanocytes after laser-abrasion for the treatment of segmental vitiligo. J. Dermatol. 27:434–439, 2000.*
Hu et al. Influence of autonomic neurotransmitters on human uveal melanocyts in vitro. Exp. Eye Res. 71:217–224, 2000.*
Hu, D.N. Regulation of growth and melanogenesis of uveal melanocytes. Pigment Cell Res. 13 Suppl 8:81–86, 2000.*
Swope et al. Long–term proliferation of human melanocytes is supported by physiologic mitogens alpha–melanotropin, endothelin–1 and basic fibroblast growth factor. Exp. Cell Res. 217:453–459, 1995.*
Bergman L, Seregard S, Nilsson B, Ringborg U, Lundell G, Ragnarsson–Olding B. Incidence of uveal melanoma in Sweden from 1960 to 1998. Invest. Ophthmol. Vis. Sci. 2002; 43, 2579–2583.
Boissy RE. Extracutaneous Melanocytes. In *The Pigmentary System*, Edited by Nordland JE et al. Oxford Univ. Press, Oxford, 1998. p. 68.
Boissy RE. The Melanocyte: Its structure, function, and subpopulations in skin, eye and hair. Dermatologic Clinics 1988; 6: 161–173.
Cohen Y, Goldberg–Cohen N, Parrella P, Chowers I, Merbs SL, Pe'er J, Sidransky D. Lack of BRAF mutation in primary melanoma. Invest. Opthalmol. Vis. Sci. 2003, 44: 2876–2878.
Chen YF, Yang PY, Liang SF, Hu DN Repigmentation of vitiligo following transplantation of autologous cultured melanocytes. Show–Chwan Med J. 1999; 1(2):85–90.
Edmunds SC, Kelsell DP, Hungerford JL, Cree IA. Mutational analysis of selected genes in the TGFβ, Wnt, pRb, and p53 pathways in primary uveal melanoma. Invest. Ophthalmol. Vis. Sci. 2002: 43: 2845–2851.
Hu DN. Regulations of growth and melanogenesis of uveal melanocytes. Pigment Cell Res 2000; 13 (Suppl. 8): 81–86.
Hu DN, Stjernschantz J, McCormick SA. Effect of prostaglandins A(2), E(1), F(2 alpha)and latanoprost on cultured human iridal melanocytes. Exp Eye Res. Jan. 2000;70(1):113–20.
Hu DN, McCormick SA, Lin AY, Lin JY. TGF–beta2 inhibits growth of uveal melanocytes at physiological concentrations. Exp Eye Res. Aug. 1998;67(2):143–50.
Hu DN, McCormick SA, Orlow SJ, Rosemblat S, Lin AY. Regulation of melanogenesis by human uveal melanocytes in vitro. Exp Eye Res. Mar. 1997;64(3):397–404.
Hu DN, McCormick SA, Orlow SJ, Rosemblat S, Lin AY, Wo K. Melanogenesis by human uveal melanocytes in vitro. Invest Ophthalmol Vis Sci. Apr. 1995;36(5):931–8.
Hu DN, McCormick SA, Ritch R, Pelton–Henrion K. Studies of human uveal melanocytes in vitro: isolation, purification and cultivation of human uvea melanocytes. Invest Ophthalmol Vis Sci. Jun. 1993;34(7):2210–9.
Hu DN, McCormick SA, Ritch R. Studies of human uveal melanocytes in vitro: growth regulation of cultured human uveal melanocytes. Invest Ophthalmol Vis Sci. Jun. 1993;34(7):2220–7.
Loercher A.E., Harbour JW. Molecular genetics of uveal melanoma. Curr. Eye Res. 2003; 27, 69–74.
Singh AD, Rennie IG, Seregard S, Giblin M, McKenzie J. Sunlight exposure and pathogenesis of uveal melanoma. Surv. Ophthalmol. 2004; 49, 419–28.
ten Berge PJ, Danen EH, van Muijen GN, Jager MJ, Ruiter DJ. Integrin expressions in uveal melanoma differs from cutaneous melanoma. Invest Ophthalmol Vis Sci 1993; 34:3635–3640.

* cited by examiner

*Primary Examiner*—David Guzo
*Assistant Examiner*—Quang Nguyen
(74) *Attorney, Agent, or Firm*—Baker Botts LLP

(57) ABSTRACT

The present invention provides methods and compositions for providing graft recipients with epidermal melanocytes. Specifically, the methods and compositions of the invention provide for populations of epidermal melanocytes that may be isolated from a patient and cultured in vitro to generate a proliferating population of epidermal melanocytes that exhibit growth, migration and melanin production. The invention is based on the discovery of a culture medium composed of natural components, for culturing epidermal melanocytes that exhibit increased proliferative capacity, migratory behaviors and melanin production. The invention provides novel in vitro methods for culturing epidermal melanocytes, including those isolated from the skin of a healthy subject, to generate a proliferating population of epidermal melanocytes. The methods and compositions of the invention may be used for transplantation to treat patients having hypopigmentation or depigmentation skin disorders.

17 Claims, 15 Drawing Sheets

EPIDERMAL MELANOCYTE CULTURE FORMULATIONS

1. INTRODUCTION

Figure 1A:
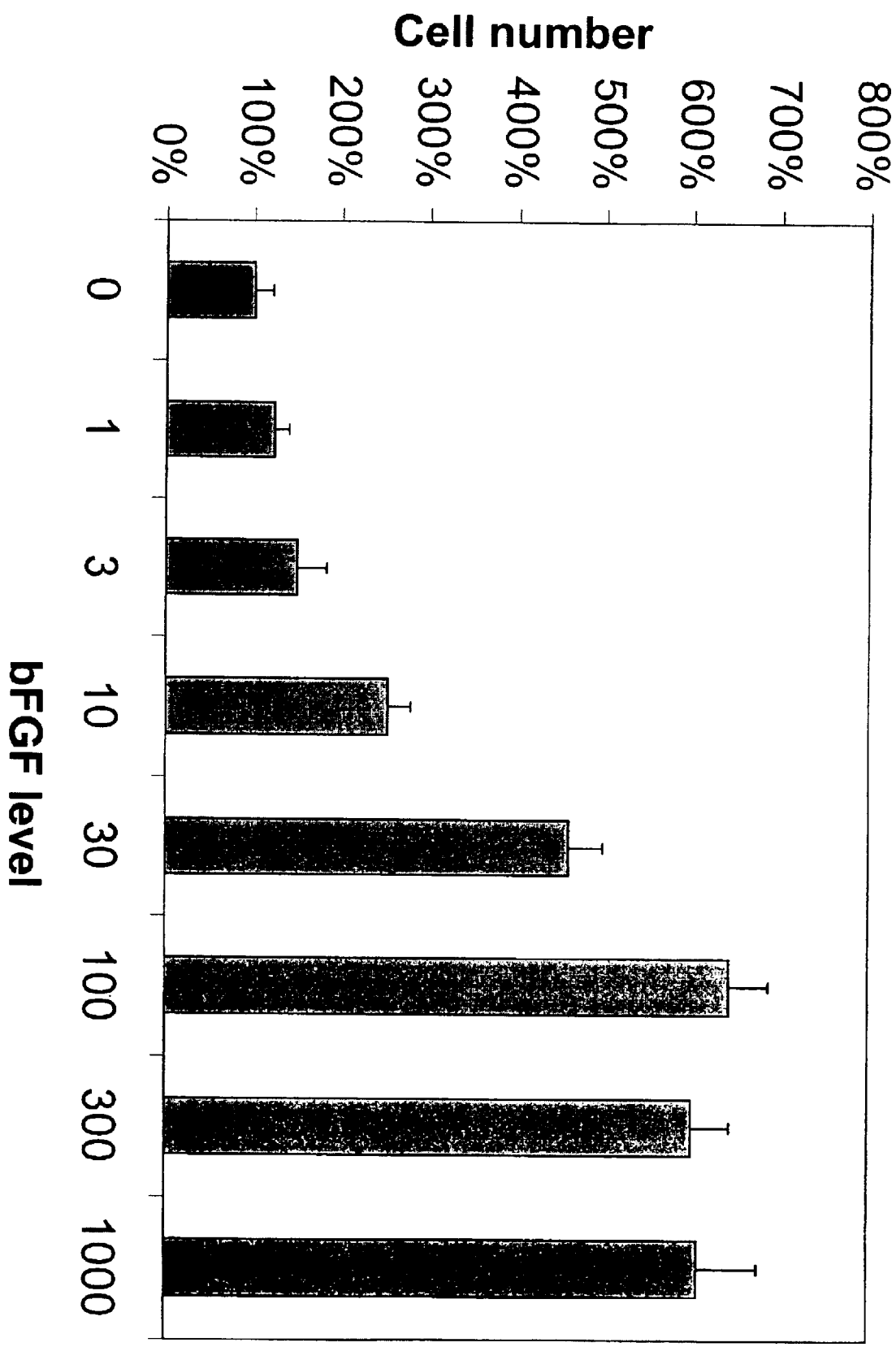

The present invention provides methods and compositions for providing graft recipients with epidermal melanocytes. Specifically, the methods and compositions of the invention provide for populations of epidermal melanocytes that may be isolated from a patient and cultured in vitro to generate a proliferating population of epidermal melanocytes that exhibit growth, migration and melanin production. The invention is based on the discovery of a culture medium composed of natural components, for culturing epidermal melanocytes that exhibit increased proliferative capacity, migratory behaviors and melanin production. The invention provides novel in vitro methods for culturing epidermal melanocytes, including those isolated from the skin of a healthy subject, to generate a proliferating population of epidermal melanocytes. The methods and compositions of the invention may be used for transplantation to treat patients having hypopigmentation or depigmentation skin disorders.

2. BACKGROUND OF THE INVENTION

Skin color is determined by a combination of the pigments produced in the skin and natural colors of the upper layers of the skin. The epidermis, which is the outer epithelial layer of the skin, contains epidermal melanocytes which produce the skin pigmentation, referred to as melanin. In patients with hypopigmentation or depigmentation of the skin, the melanocytes in the skin are absent, destroyed or non-functional. As a result, white patches of skin appear on different parts of the body.

Pigmentation is not only a protective function of the melanocytes, but also plays an important role in cutaneous aesthetics. Hypopigmentation or depigmentation of the skin results from specific disorders or conditions affecting the pigmentation system through either local destruction or absence of melanocytes or through inhibition of their function. Although this situation is clinically benign, the psychological and social consequences can be debilitating.

Vitiligo is a specific skin pigment disorder characterized by the destruction of epidermal melanocytes and development of patchy depigmented lesions. Current treatments, which include the use of photosensitizes (e.g. psoralens) with UVA radiation (PUVA) or topical corticosteroids, have low success rates and are generally accompanied by unpleasant side effects (Shaffali and Gawkrodger, 2000, Clin Exp Dermatol 25:575).

Surgical skin grafting techniques have been applied to patients with vitiligo, including transplantation of blister tops or minigrafts from normal skin (Koga et al., 1988, Arch Dermatol. 124:1656; Gupta et al., 1999, Dermatol Surg 25:955; Falabella, 1984, J Dermatol Surg. Oncol. 10:136; Suvanprakorn et al., 1985, J Am Acad Derm 13:968; Sarkar et al., 2001, J Dermatol 28:540; Pai et al., 2002 J. Eur Acad Dermatol Venereol 16:604). These treatments have been successful where the area of the lesion is small and localized. However, in individuals who have either large depigmented patches or many depigmented patches, it is difficult to obtain enough graft to cover all the lesions (Van Geel, N. et al., 2001, Dermatology 202:162).

In order to achieve success in autologous skin transplants for large areas of the skin, it is often necessary to obtain skin grafts with large number of cells, in particular melanocytes. Alternatively, one can expand a population of autologous melanocytes in culture for transplantation. This approach entails obtaining a population of melanocytes from the patient, culturing this population of cells in vitro under conditions that promote cell proliferation, cell migration and production of melanogenesis, and reintroducing the cells to the patient's skin under conditions that promote repigmentation.

A number of different factors have been found to stimulate the growth of melanocytes in culture. For example, hepatocyte growth factor (HGF) is a pleiotrophic growth factor family initially identified as a potent mitogen for cultured hepatocytes. HGF has been shown to stimulate growth and migration of various epithelial cells and vascular endothelial cells (Matsumoto et al., 1996, J. Biochem. 119:591; Jiang et al., 1997, Histol Histopathol 12:537). In addition, it has been shown that HGF stimulates growth of cultured ocular melanocytes (Hu, 2000, Pigment Cell Res 13 (Suppl. 8): 81) and in skin, HGF can be produced by the fibroblasts in the dermis (Halaban et al., 1993, Ann New York Acad Sci 680:290).

α-Stimulating Factor (αMSH) is a tridecapeptide with a sequence identical to the first 13 amino acids of adrenocorticotropin (ACTH). Keratinocytes appear to be a major source of the peptide (Thody et al., 1998, Pigment Cell Res 11:265; Wakamatsu et al., 1997, Pigment Cell Res 10:288). Previous reports on the effect of αMSH on cultured epidermal melanocytes have been conflicting (Halaban et al., 1988, J Cell Biol 107:1611; Thody and Graham., 1998, Pigment Cell Res 11:265; Wakamatsu et al., 1997, Pigment Cell Res 10:288; Abdel-Malek et al., 1995, Proc. Natl. Acad. Sci USA 92:1789). For example, Halaban et al., reported that αMSH failed to stimulate growth on cultured epidermal melanocytes (Halaban et al., 1988, J Cell Bol 107:1611). However, the lack of a response in these studies may be related to the addition of cholera toxin to the media.

Epinephrine is a potent stimulator of both α- and β-adrenergic receptors. Epinephrine activates the β2-adrenergic receptors through the cAMP second messenger system to stimulate melanocytes. β2-adrenergic agonists stimulate growth and melanogenesis of ocular melanocytes and α-, β1- and β3-adrenergic agonists did not have any effect on growth or melanogenesis (Hu et al., 2000, Exp. Eye Res. 71:217).

Lerner et al. (1987, J Invest Derm 89:219) described the use of melanocyte transplantation for the treatment of piebaldism, a genetic disorder characterized by congenital patches of white skin and hair that lack melanocytes. A small piece of skin was obtained from the patient by shave biopsy and the epidermal melanocytes were cultured using a culture medium containing TPA (12-O-tetradecanoyl-phorbol-13-acetate), IBMX (3-isobutyl-1-methylxanthine), cholera toxin and newborn calf serum. Though cells were successfully transplanted to an area of hypopigmentation, the use of TPA, a well-known tumor promoting factor, in the medium discourages its applications in human transplantations.

U.S. Pat. No. 4,757,019 also discloses the use of a culture medium for culturing human melanocytes. This medium comprises MEM, a basal medium, with 5% fetal bovine serum, phorbol 12-myristate13-acetate (PMA, also known as TPA 10 ng/ml) and cholera toxin ($10^{-8}$ M). Since this medium also contains toxic compounds, i.e., PMA and cholera toxin it would not be appropriate for applications in human transplantation.

Olsson and Juhlin (1992, Lancet 340:981) reported the use of an epidermal melanocyte culture medium which was a formulation containing PC-1, supplemented with basic fibroblast growth factor (bFGF), dbcAMP, penicillin and streptomycin. The culture medium was used to expand isolated epidermal melanocytes for use in autologous melanocyte transplantation. This medium did not contain any serum, which is necessary for the growth and differentiation of epidermal melanocytes. In addition, the concentration of bFGF (5 ng/ml) in the medium was too low to stimulate adequate growth of epidermal melanocytes. Furthermore, the dbcAMP added to the medium is not a natural substance and only acts for a short period of time. In addition, no quantitative data on the number of cellular divisions and melanin content of the expounded cells have been reported, therefore, it is difficult to evaluate the efficiency of this medium. It is noteworthy, however, that Olsson and Juhlin later described the use of a non-cultured epidermal melanocyte transplantation method for the treatment of vitiligo (Olsson and Juhlin, 1998, Br J Dermatol 138:644).

Additional culture media, e.g., HU16 (FIC medium) has been developed for culturing epidermal melanocytes. HU16 medium comprises F12 medium, a commercially available basal medium, supplemented with an optimal concentration of bFGF, 3-isobutyl-1-methxanthine (IBMX), cholera toxin and fetal bovine serum. This medium has been used successfully to grow epidermal melanocytes for melanocyte transplantation treatment of vitiligo in over 120 patients in Taiwan. (Chen et al., 1999, Show Chwan Med J 1:85; Chen et al., 2000, J. Dermatol 27:434; Chen et al., 2001, J Am Acad Dermatol 44:545)

Although the HU16 medium stimulated a great increase in melanocyte growth, the disadvantages of this medium include that (i) the IBMX and cholera toxin contained in this medium are non-physiological, non-natural substances and cholera toxin has negative psychological implications for physicians and patients, and (ii) the growth and melanogenesis stimulating effects of this medium, although better than for any previously reported media, is not optimal. Thus, some patients may wait for prolonged periods of time for the cells to grow and a small percentage of patient's cells fail to ever grow well enough to meet the requirement of transplantation. Moreover, even with a successful transplant, some patients have a lack of pigmentation at the periphery of the transplanted region, possibly due to insufficient stimulation of cell migration provided by this medium (Chen et al. 1999, Show Chwan Med J 1999 1:85; Chen et al., 2000, J. Dermatol 27:434).

The requirements for medium useful for clinical cell transplantation are different from those of regular culture medium. For example, medium for clinical cell transplantation should contain all natural, physiological substances, so that it will not damage the cell or pose a risk of harm to the patient after cell transplantation. Furthermore, the culture medium should provide for cell growth, melanogenesis and migration. None of the previously reported culture media use for epidermal melanocyte transplantation has been found to meet these criteria, nor have quantitative tests of the effects of all these culture media on cell growth, melanogenesis and migration have not been reported.

Therefore, there is a need to develop novel compositions comprising non-toxic and/or natural and/or physiologically compatible components and methods of culturing epidermal melanocytes in vitro under conditions that promote epidermal melanocyte proliferation, as well as stimulate normal epidermal melanocyte cell properties, including melanin production and cell migration.

3. SUMMARY OF THE INVENTION

The present invention provides novel compositions and methods for culturing epidermal melanocytes. The methods and compositions of the present invention may be used to provide skin pigmentation to patients having skin disorders characterized by a lack of skin pigmentation. Such disorders include but are not limited to vitiligo or loss of skin pigmentation due to skin diseases such as inflammation, chemical or physical damage. In addition, the methods of the invention may be used in combination with dermabrasion techniques for cosmetic purposes.

The compositions of the invention relate to a culture medium comprising a basal medium, supplemented with serum, growth factors, and agents designed to elevate cAMP levels. In addition, the present invention relates to compositions comprising epidermal melanocytes cultured in a medium comprising a basal medium, supplemented with serum, growth factors and agents designed to elevate cAMP levels.

The present invention further relates to methods of culturing epidermal melanocytes for transplantation using the medium of the present invention to obtain a proliferating population of epidermal melanocytes that is capable of migratory behavior and melanogenesis. The invention is based on the observation that epidermal melanocytes cultured in the medium of the present invention possess quantitatively enhanced proliferation, migration and melanogenesis capabilities.

The present invention provides grafting methods of treating skin pigmentation disorders utilizing cultured epidermal melanocytes, comprising (1) isolating epidermal melanocytes from an individual, (2) culturing the epidermal melanocytes in the medium of the invention to obtain an expanded population of epidermal melanocytes with enhanced proliferative, migratory and melanogenesis capabilities, and (3) transplanting the expanded culture of epidermal melanocytes onto the individual's skin.

In a specific embodiment of the invention, cultured epidermal melanocytes may be genetically engineered, prior to transplantation, to enable them to produce a wide range of proteins, including but not limited to, growth factors, cytokines, extracellular matrix proteins, or other biologically active molecules. In this way, any new tissue derived from the transplanted epidermal melanocytes will produce the desired biologically active protein.

The present invention, which relates to a culture medium system with natural and physiological components, provides a more physiological micro-environment for incubation of epidermal melanocytes. In addition to serving as a source of cells for transplantation, the culture medium system of the invention provides an in vitro model system for testing the effects of various biological substances (e.g., drugs, herbs and cosmetics, etc.) on the growth, melanogenesis, migration ability and other functions of epidermal melanocytes.

4. BRIEF DESCRIPTIONS OF THE DRAWINGS

Figure 1B:
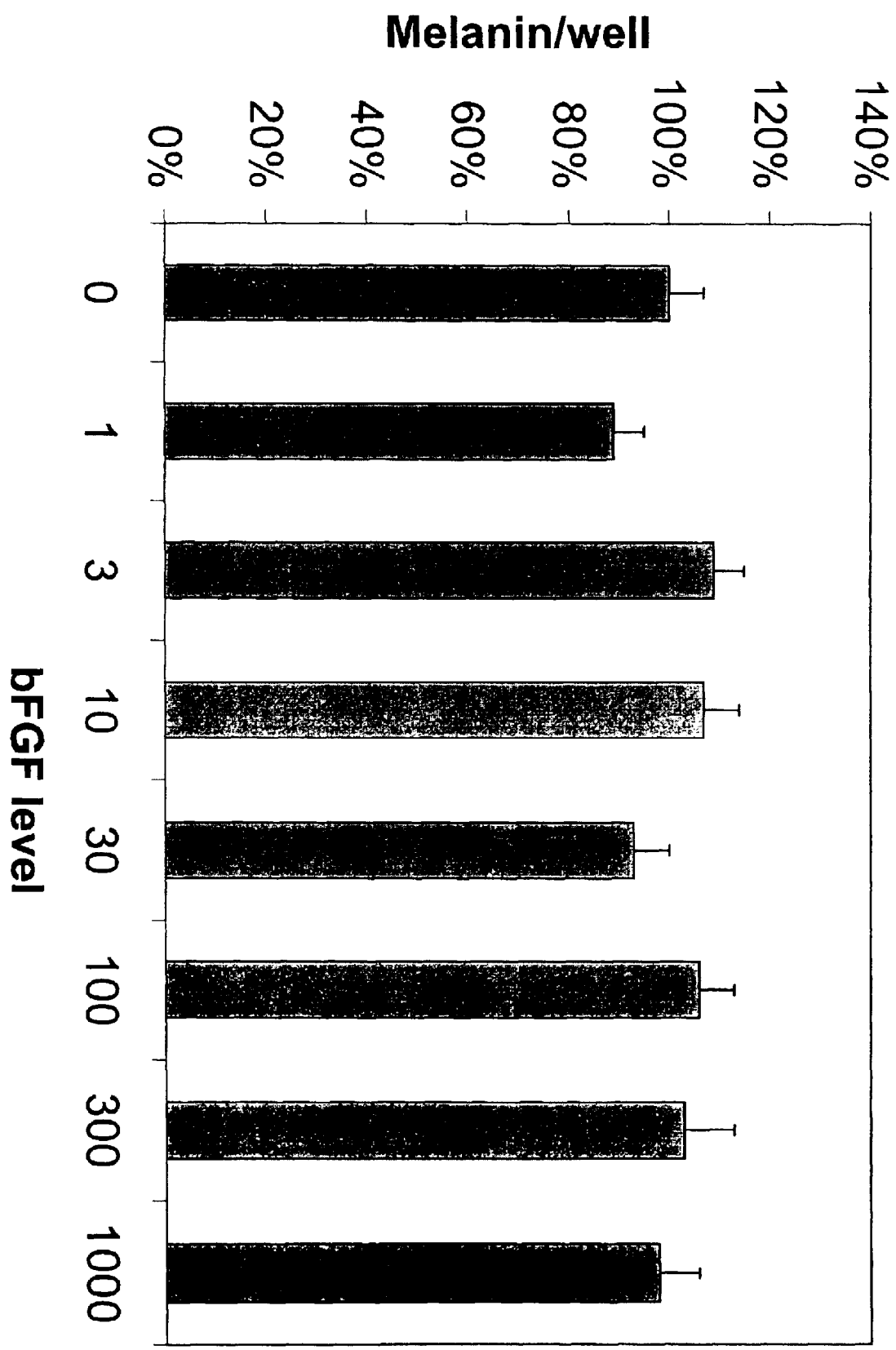

FIGS. 1A–B. Effects of bFGF (ng/ml) on cultured epidermal melanocytes. Cells were cultured with growth factor-deleted culture medium (control) or supplemented with various concentrations of bFGF (ng/ml) and cultured for 6 days. Cell number was counted and melanin/well was measured and compared with the controls. The results are expressed as the percentages of the controls (3 wells in each group, Mean±SD). FIG. 1A. Cell growth. FIG. 1B. Melanin content.

Figure 2A:
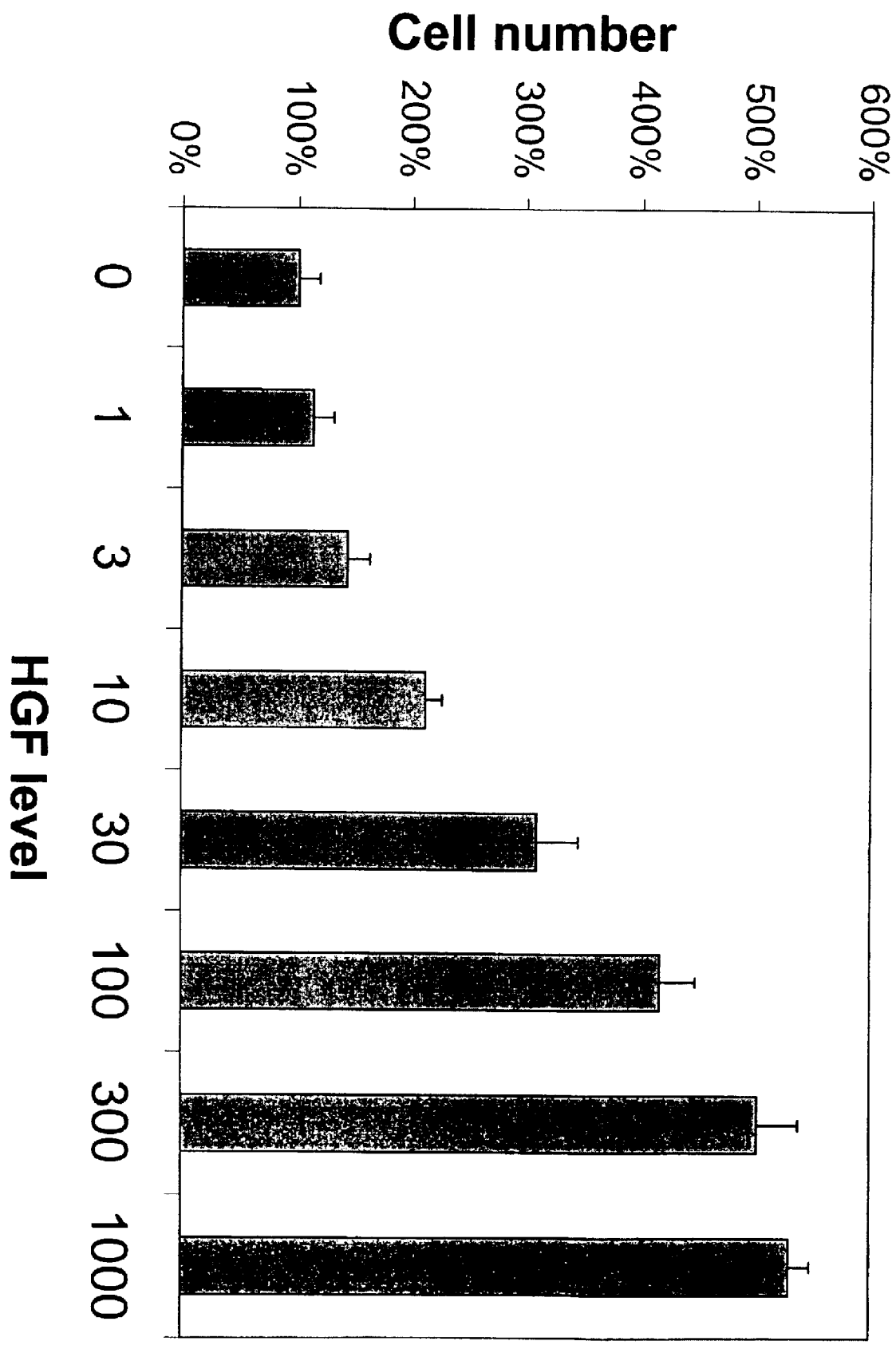
Figure 2B:
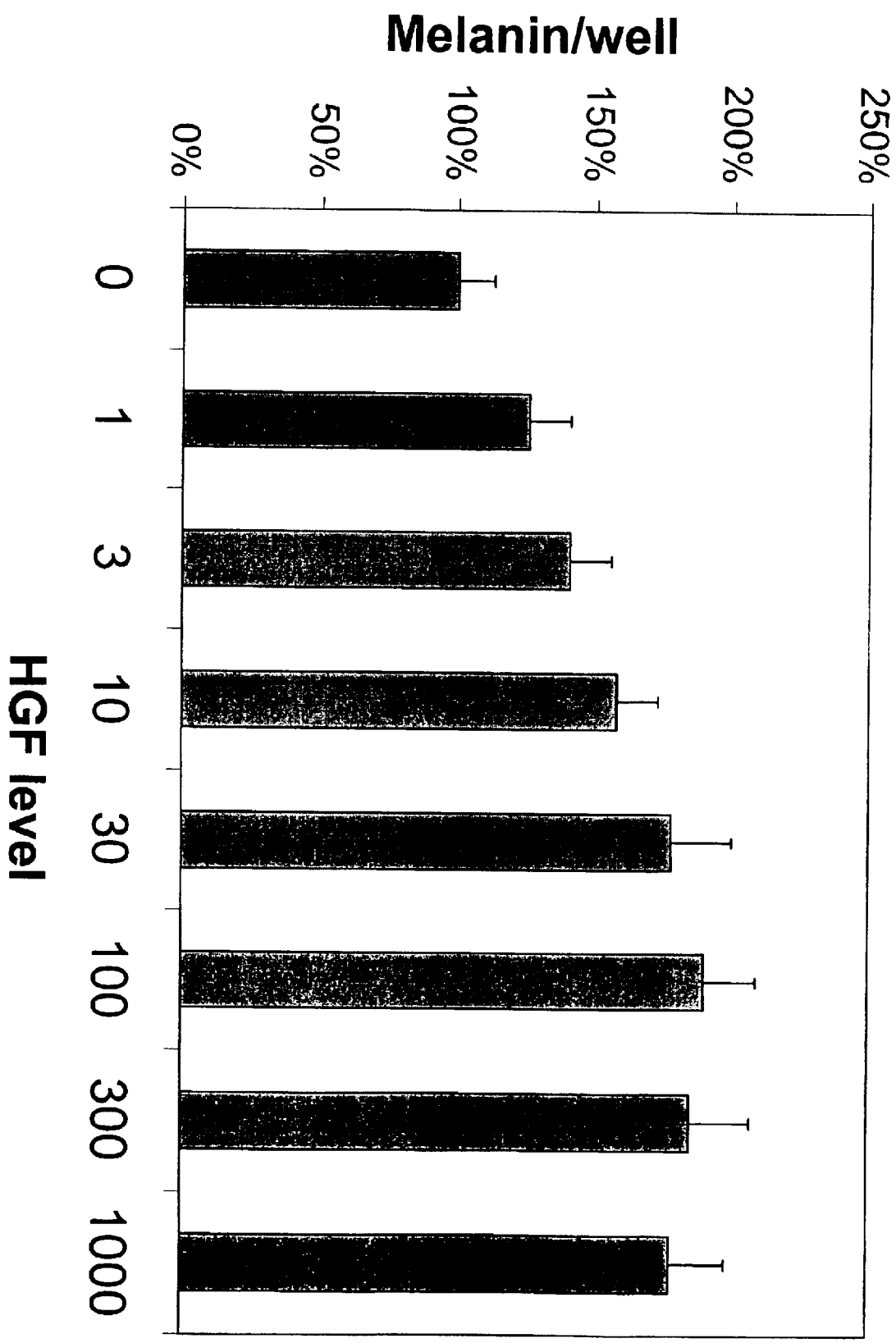
Figure 2C:
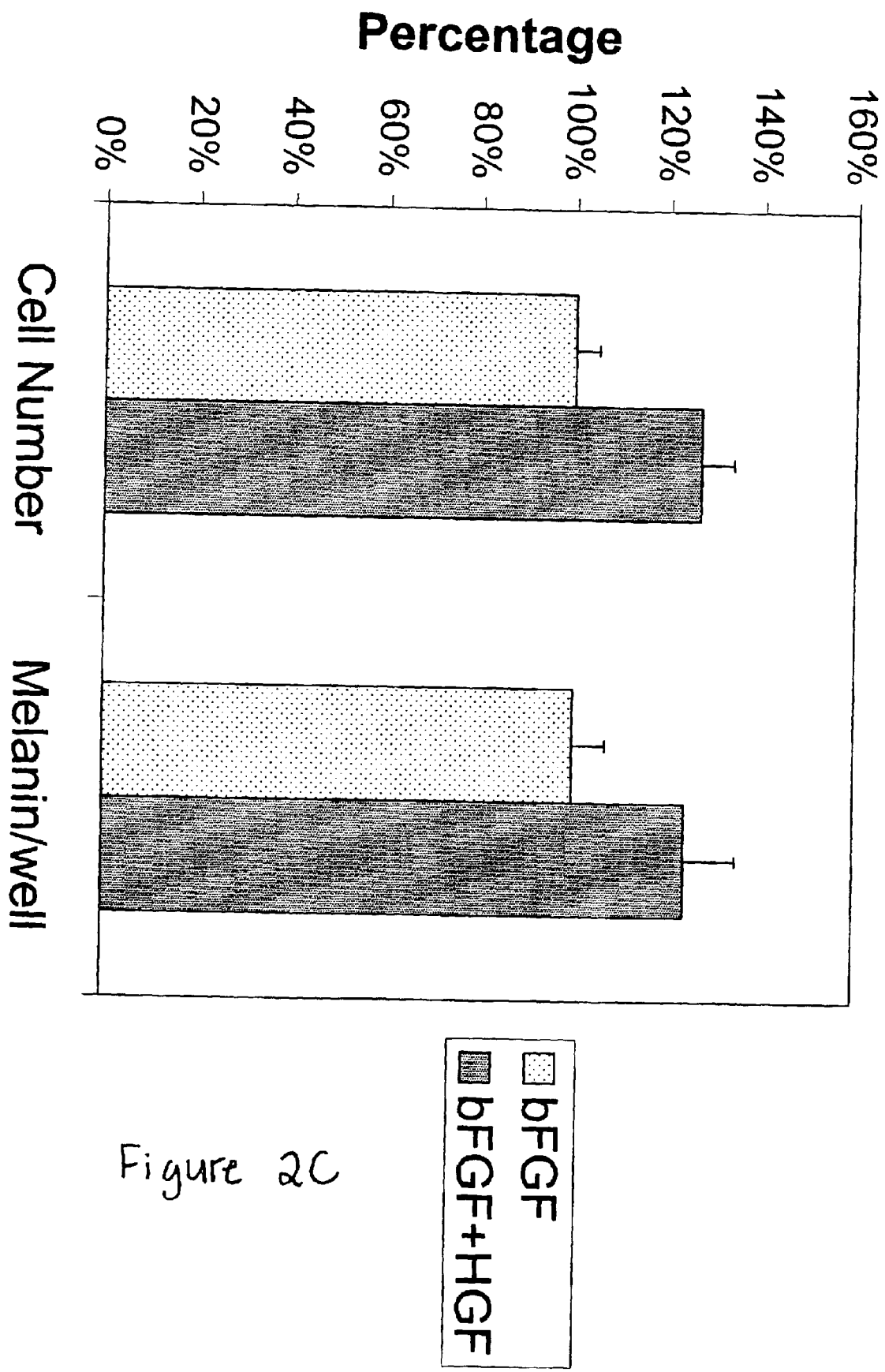
Figure 2D:
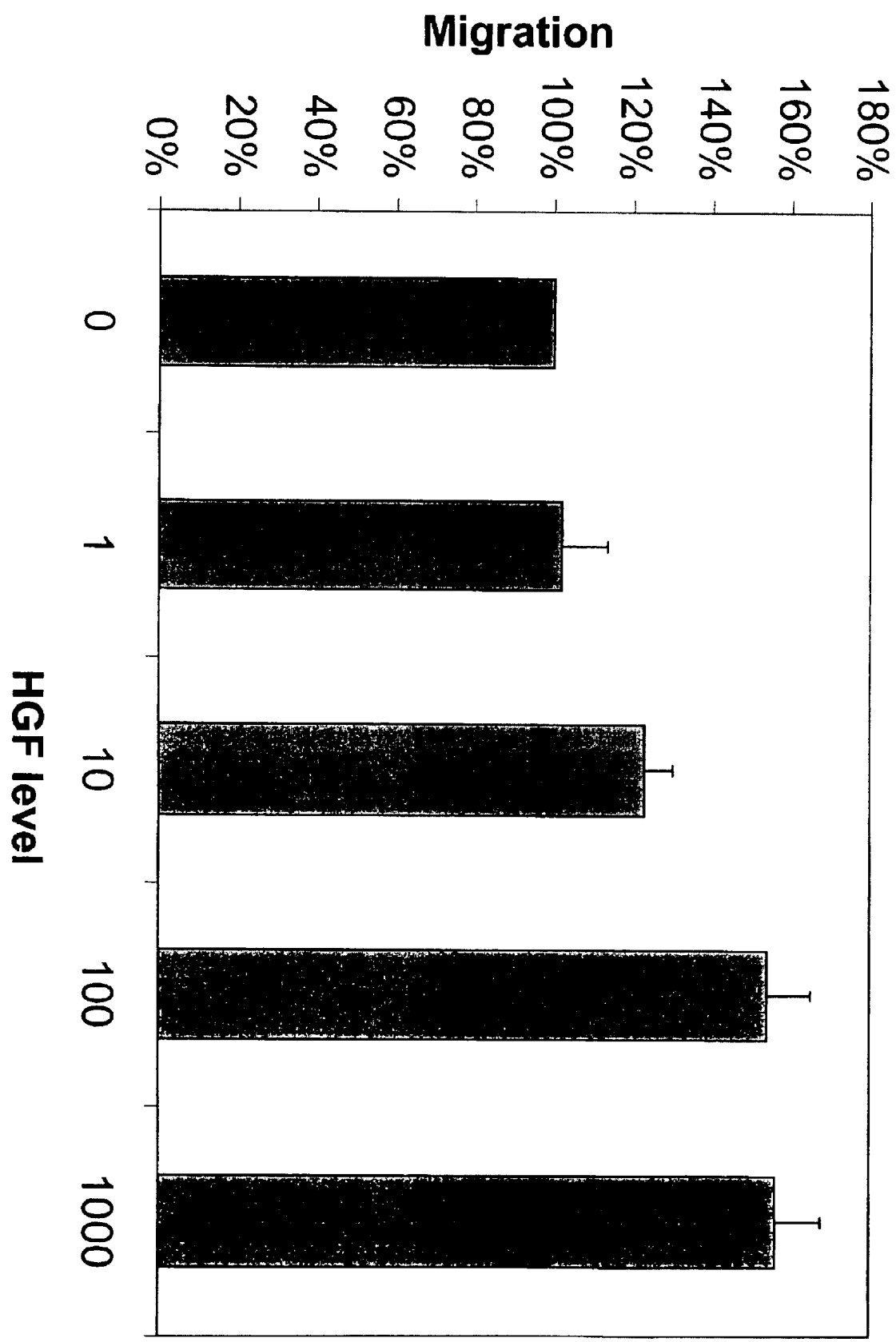

FIGS. 2A–D. Effects of HGF on cultured epidermal melanocytes. Cells were cultured with growth factor-deleted culture medium (control) or supplemented with various concentrations of HGF (ng/ml) and cultured for 6 days. Cell number was counted and melanin/well was measured and compared with the controls. The results are expressed as percentages of the controls (3 wells in each group, Mean±SD). FIG. 2A. Cell growth. FIG. 2B. Melanin content. FIG. 2C. Comparison of epidermal melanocytes cultured with bFGF (25 ng/ml) alone or bFGF with HGF (100 ng/ml). FIG. 2D. Effect of HGF on migration of epidermal melanocytes. The results are expressed as the percentages of the controls (3 wells in each group, Mean±SD).

Figure 3A:
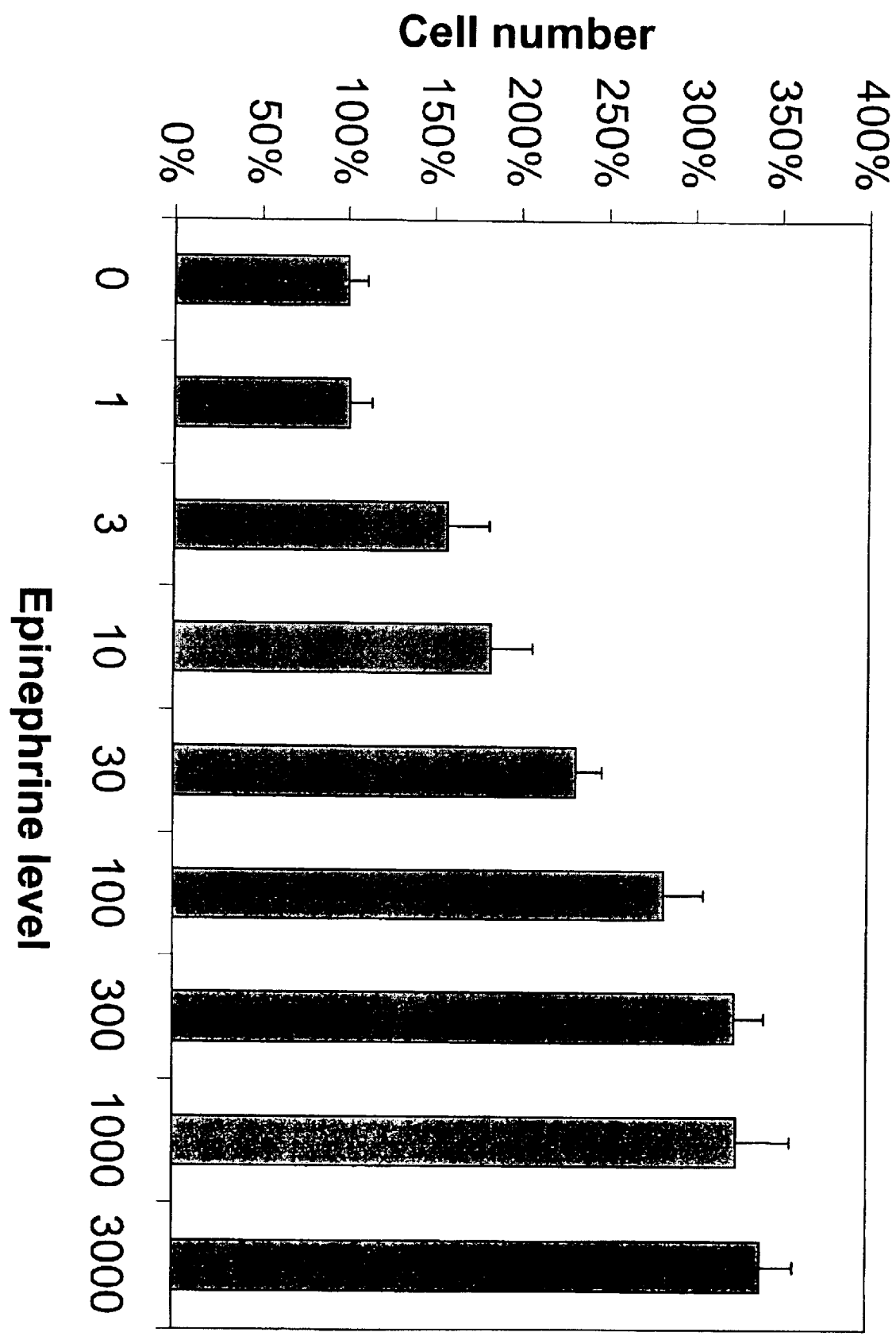
Figure 3B:
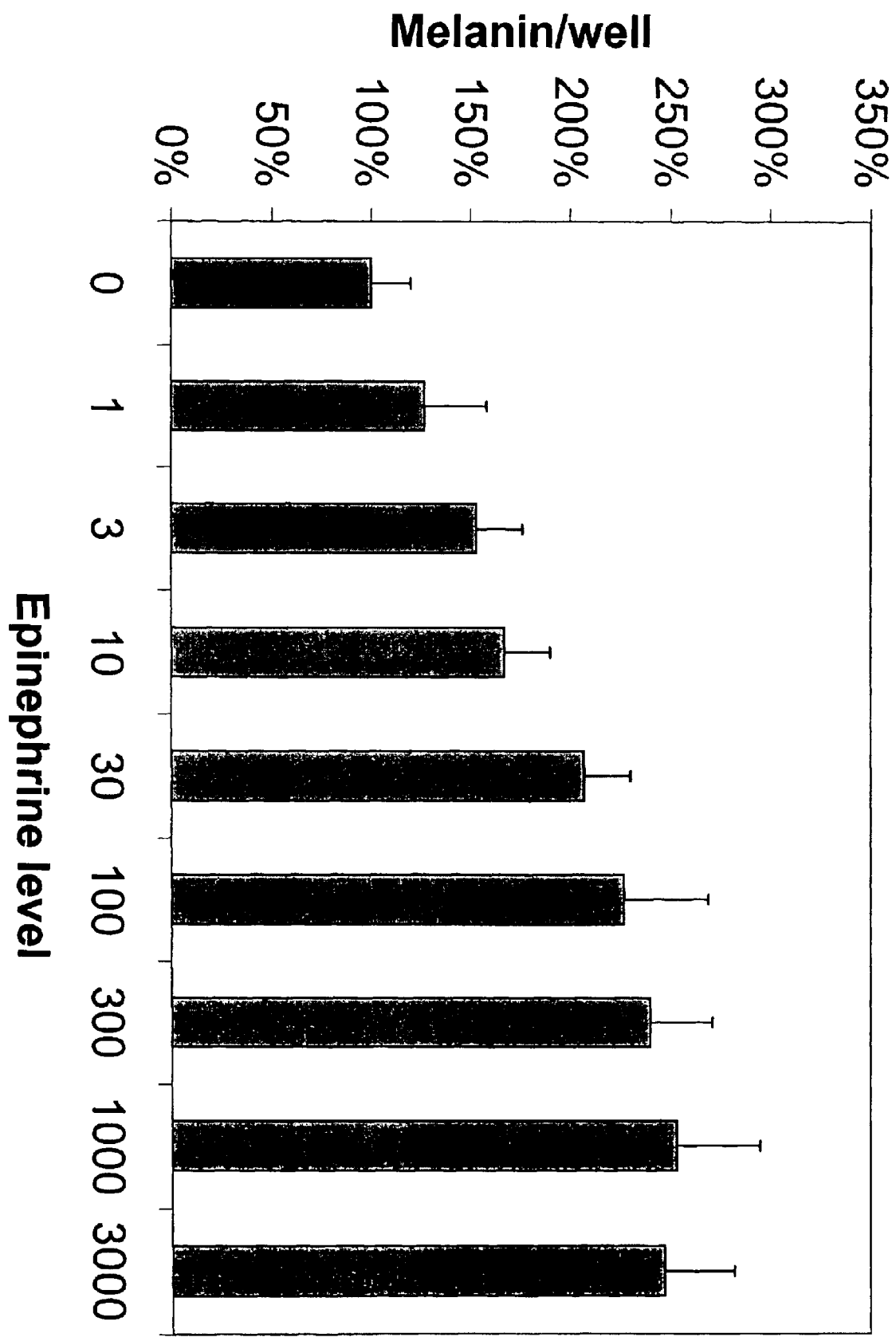

FIGS. 3A–B. Effects of epinephrine on cultured epidermal melanocytes. Cells were cultured with cAMP-elevating agents-deleted culture medium (control) or supplemented with various concentrations of epinephrine (ng/ml) and cultured for 6 days. Cell number was counted and melanin/well was measured and compared with the controls. The results are expressed as the percentages of the controls (3 wells in each group, Mean±SD). FIG. 3A. Cell growth. FIG. 3B. Melanin content.

Figure 4A:
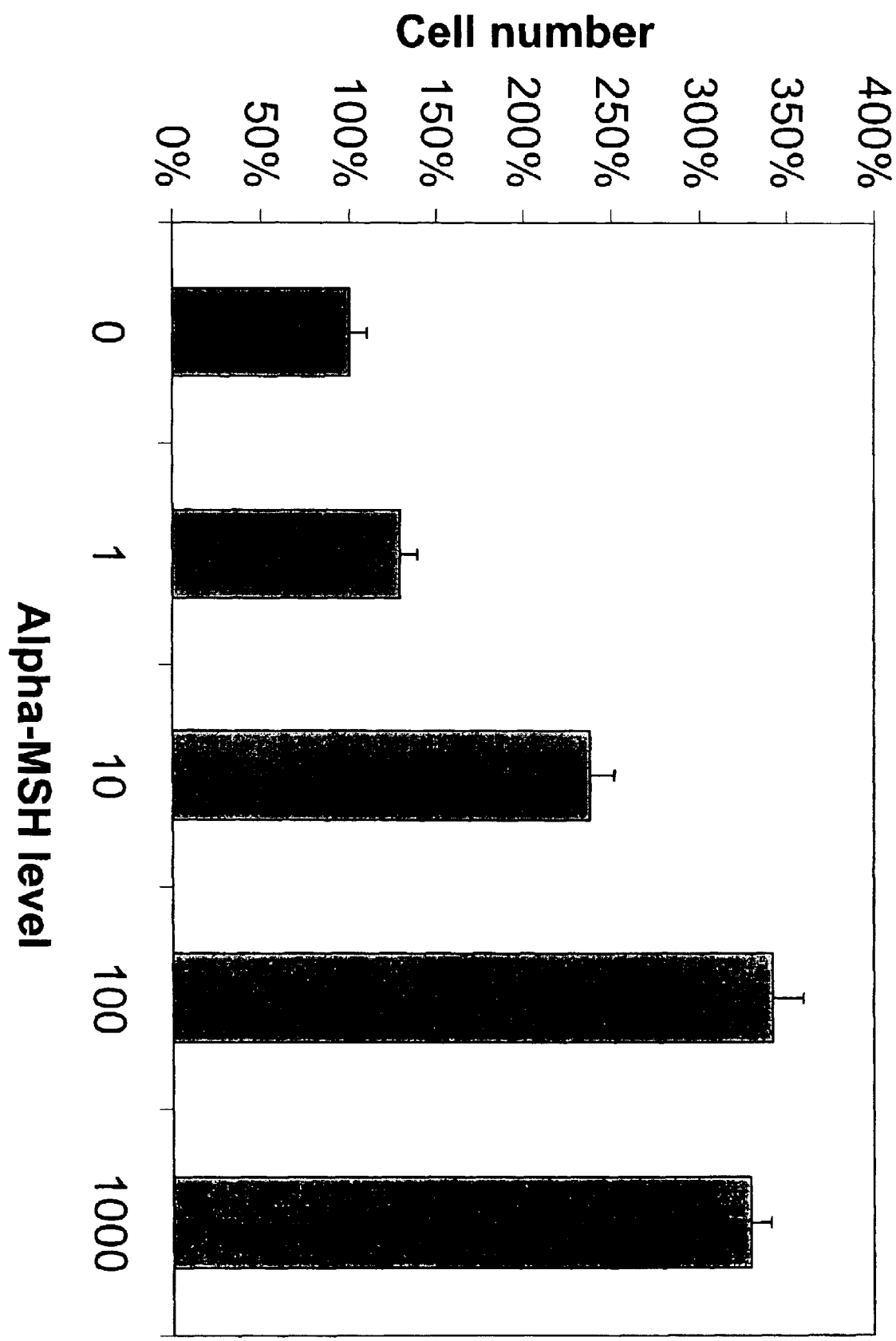
Figure 4B:
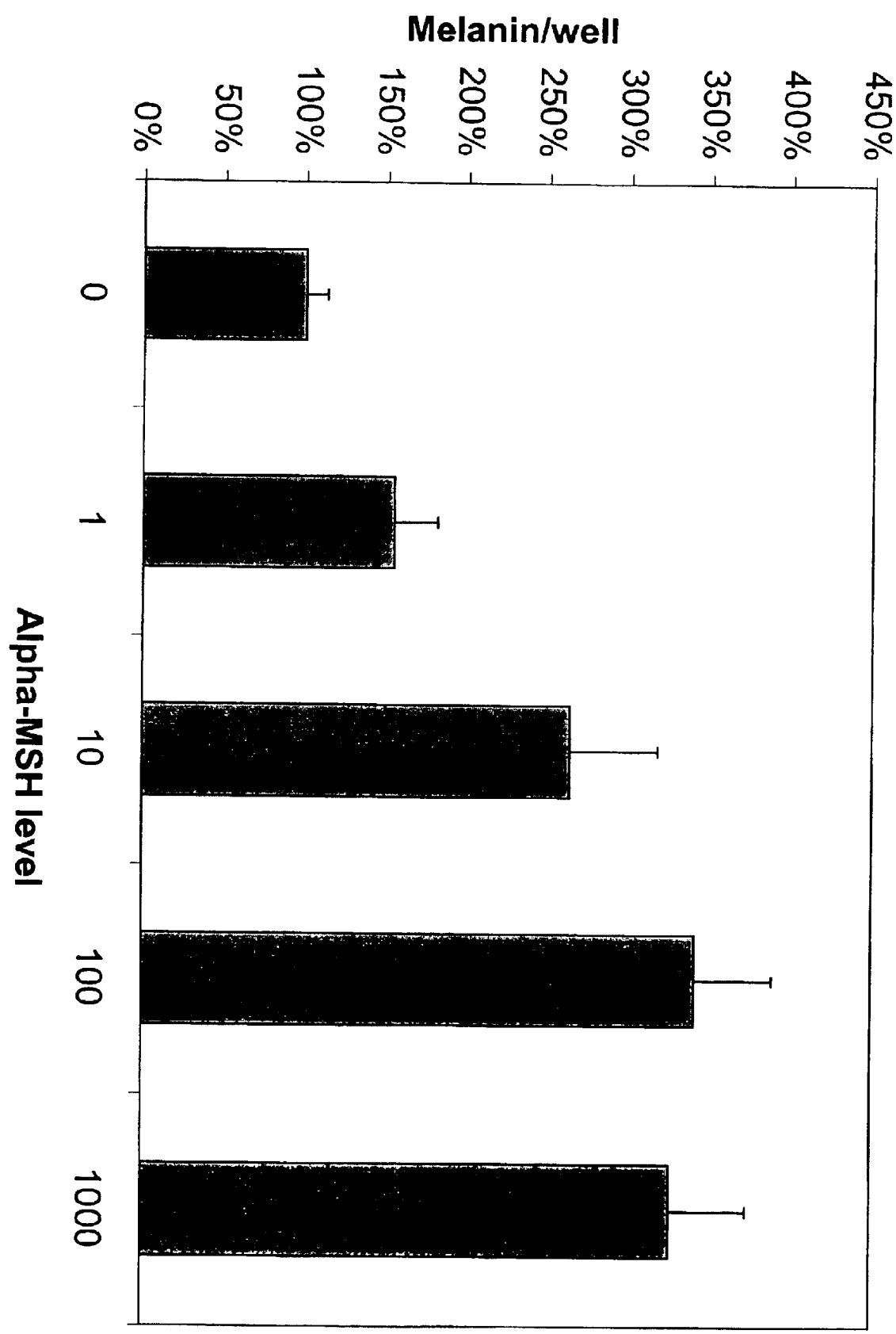

FIGS. 4A–B. Effects of α-MSH on cultured epidermal melanocytes. Cells were cultured with AMP-elevating agents-deleted culture medium (control) or supplemented with various concentrations of α-MSH (ng/ml) and cultured for 6 days. Cell number was counted and melanin/well was measured and compared with the controls. The results are expressed as the percentages of controls (3 wells in each group, Mean±SD). FIG. 4A. Cell growth. FIG. 4B. Melanin content.

Figure 5A:
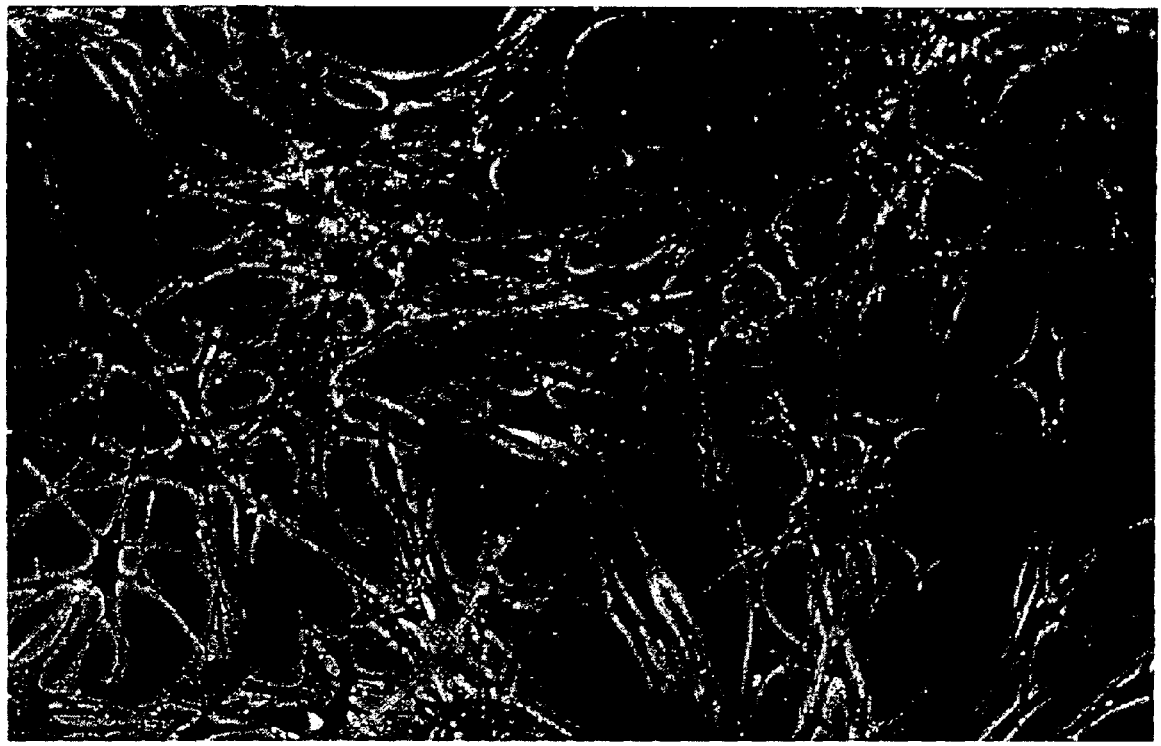
Figure 5B:
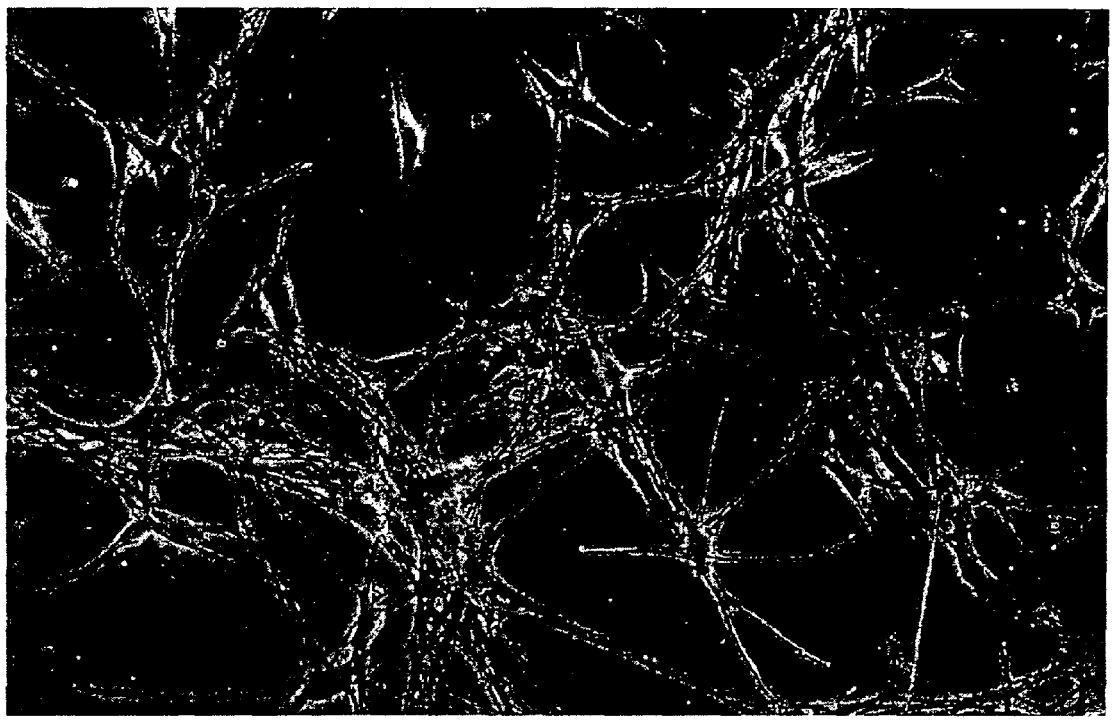
Figure 5C:

FIGS. 5A–C. Epidermal melanocytes cultured with various culture media (phase-contrast microscopy, ×200). FIG. 5A. Cultured with Hu74 medium. FIG. 5B. Cultured with Hu16 medium. FIG. 5C. Cultured with Olsson's medium.

Figure 6:
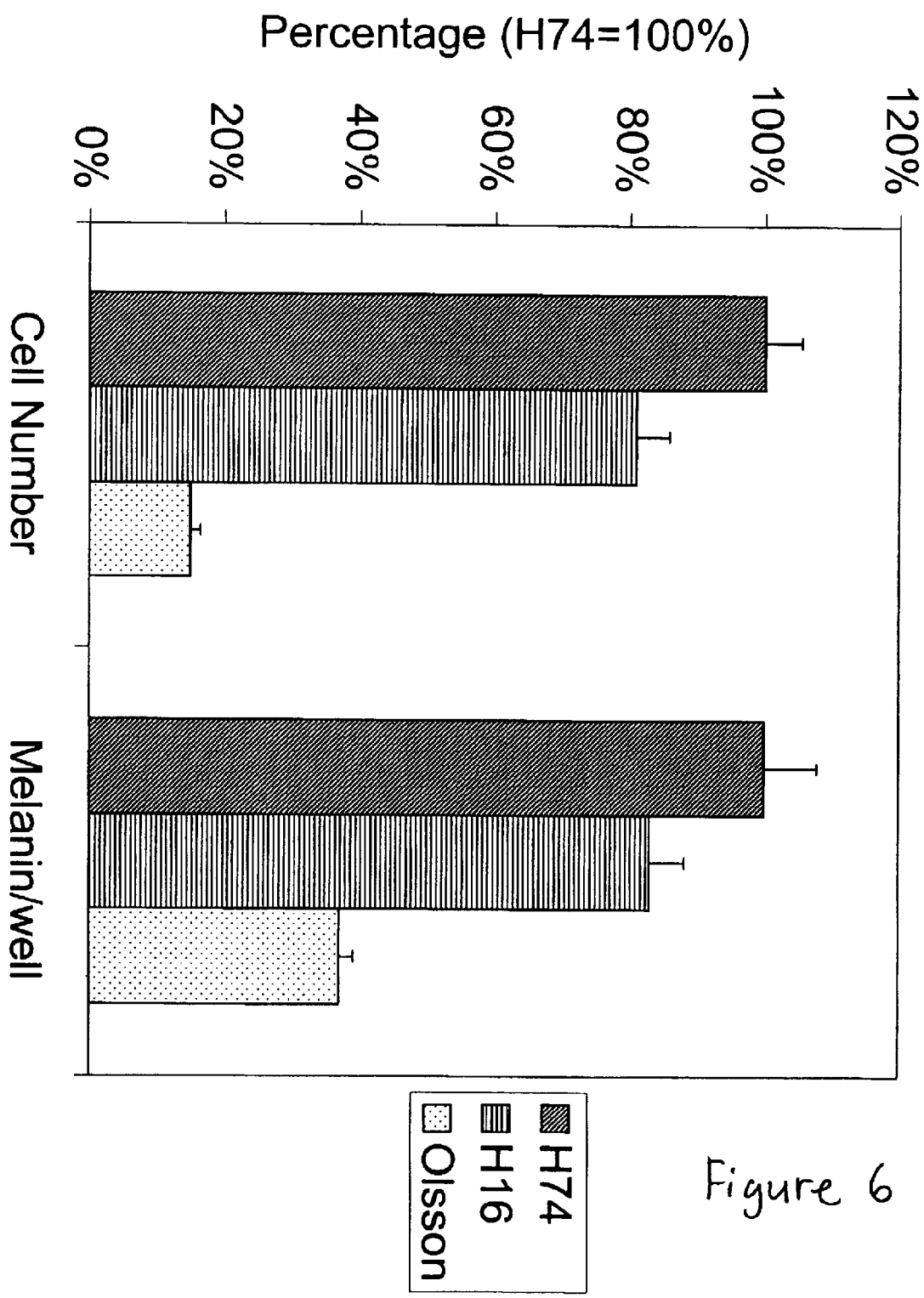

FIG. 6. Comparison of epidermal melanocytes cultured with various culture media (Hu74 medium, Hu16 medium and Olsson's medium). Cells were cultured with various culture media for 6 days. Cell number was counted and melanin/well was measured and compared. The results are expressed as the percentages of the H74 group (3 wells in each group Mean±SD).

Figure 7:
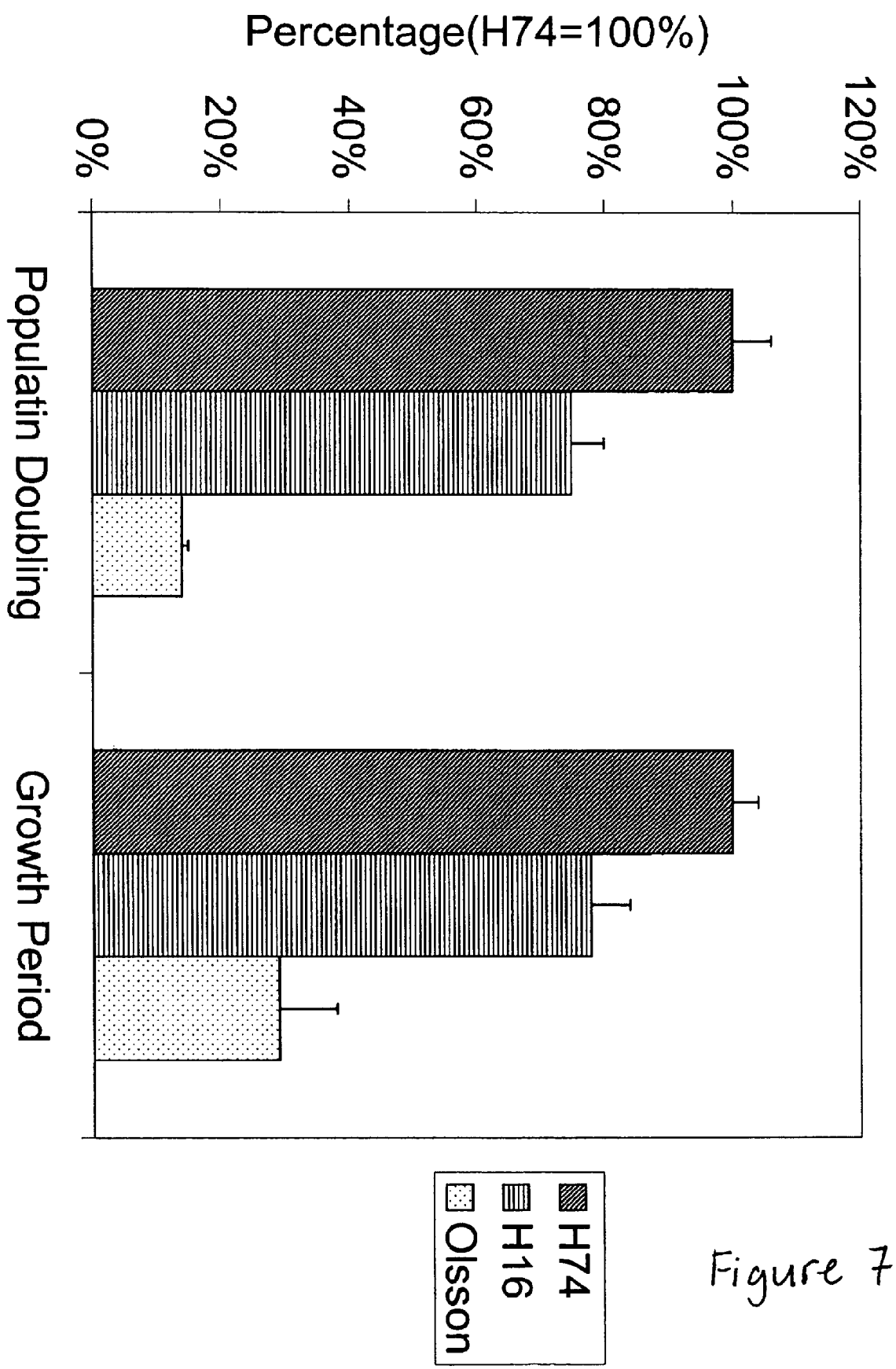

FIG. 7. Comparison of various media on their long-term effects on cell growth of cultured epidermal melanocytes. In 3 cell lines of epidermal melanocytes, cells were seeded into 3 flasks at the first subculture and cultured with Hu74, Hu16 and Olsson's medium, separately. Cells were incubated and subculture until senescence. Population doubling and period of culture before senescence were expressed as the percentages of the Hu74 group (3 cell lines in each group, Mean±SD).

5. DETAILED DESCRIPTION OF THE INVENTION

The present invention provides novel compositions and methods for culturing epidermal melanocytes and the use of such melanocytes in skin grafts. Specifically, the methods and compositions of the invention may be used to treat skin pigmentation disorders resulting from destruction of epidermal melanocytes or loss of epidermal melanocyte functions. The compositions of the invention relate to a culture medium comprising basal medium, supplemented with serum, growth factors, and cAMP-elevating agents. The medium of the invention differs from previously described medium in that it contains only natural, physiological agents. The present invention is based on the observation that epidermal melanocytes isolated and cultured in the medium of the present invention have enhanced proliferation, migration and melanogenesis.

5.1 Isolation and Culturing of Epidermal Melanocytes

Epidermal melanocytes may be obtained from a variety of different donor sources. In a preferred embodiment, autologous epidermal melanocytes are obtained from the subject who is to receive the melanocytes. This approach is especially advantageous since the immunological rejection of foreign tissue and/or a graft versus host response is avoided. In yet another embodiment of the invention, allogenic epidermal melanocytes may be obtained from donors who are genetically related to the recipient and share the same transplantation antigens on the surface of their melanocytes. Alternatively, if a related donor is unavailable, melanocytes from antigenetically matched donors may be used. Furthermore, because melanocytes do not express HLA antigen even allogenic melanocyte transplantation is possible.

Epidermal melanocytes may be obtained from the skin using a variety of different methods. The cells are derived from pigmented areas of the body and preferably from the subject in need of the skin graft. Epidermal melanocytes may be obtained from a superficial skin biopsy. One or more shave biopsies of the skin are taken from normal skin area after local anesthesia with 0.5%–1% lidocaine. Various skin graft instruments (e.g., a skin graft knife with a razor blade) can be used to take the biopsy (Loentz et al., 1994, J Am Acad Dermatol 30:591).

Epidermal melanocytes may also be obtained from a suction blister. Blisters may be produced by applying a vacuum of 300–400 mmHg to the surface of the skin for 30–90 minutes. The blisters may be 100–250 $mm^2$. The tops of the blisters are then excised and processed for culturing (Chen et al., 2000, J Dermatol 27:434). Alternatively, blisters may be produced by freezing with liquid nitrogen (Suvanprakon et al., 1985, J Am Acad Dermatol 13:968).

Epidermal sheets may be dissociated mechanically and/or treated with digestive enzymes and/or chelating agents that weaken the connections between neighboring cells, making it possible to disperse the individual cells (Chen et al., 2000, J Dermatol 27:434). Enzymatic dissociation can be carried out by treating the skin tissue with any of a number of digestive enzymes. Such enzymes include, but are not limited to, trypsin, chymotrypsin, collagenase, elastase and/or hyaluronidase. Chelating agents include, but are not limited to, EDTA. The basal layer may be teased away gently with forceps to dissociate cells from the tissue.

The cell suspension may be rinsed in medium or buffer and centrifuged one or more times to remove dissociated cells from tissue. Following preparation of a single cell suspension, the cells are cultured in the medium of the invention. In a preferred embodiment of the invention, the cell suspension may be grown in culture to inhibit the growth of keratinocytes and fibroblasts by the addition of geneticin (Halaban et al., 1984, In Vitro 20:447).

The present invention relates to a novel culture medium, referred to herein as Hu74 Medium, for use in culturing epidermal melanocytes. The medium of the invention differs from previously described medium in that it contains only natural, physiological agents.

The media of the invention comprises basal medium supplemented with serum, growth factors, and cAMP elevating agents. The basal medium may be any of the standard culture medium that provides the minimal requirements to sustain the growth of cells in culture. Such basal media, include but are not limited to basal amino acid/salt mixtures such as Ham's F12, RPMI, or DMEM. Serum is added to the media in concentrations of approximately 5–30%. Any type of animal serum may be used, including but not limited to, fetal calf, calf or human serum. Additional additives to the medium may include, for example, glucose, glutamine, vitamins and any additional additives known to those of skill in the art.

Growth factors and cytokines to be added to the basal medium include hepatocyte growth factor (HGF) and fibroblast growth factors (FGFs) such as bFGF. The present invention is based on the observation that HGF is a potent stimulator of epidermal melanocyte migration. This effect can induce transplanted epidermal melanocytes to migrate to the margin of transplanted area, which is important for decreasing the hypopigmentation at the margin of the transplanted area in patients.

Furthermore, the addition of both HGF and bFGF to the medium was found to enhance the proliferation of epidermal melanocytes indicating that HGF has an additive growth stimulating effect in conjunction with the bFGF. Thus, addition of HGF to the medium of the invention can further stimulate the growth of epidermal melanocytes in vitro, thereby shortening the patient's waiting time period for the transplantation. Further, in patients wherein epidermal melanocytes do not grow well and where the in vitro expansion of cell number required for transplantation cannot be met, HGF can be added to improve the growth of cells thereby facilitating transplantation.

In an embodiment of the invention, the culture medium of the invention contains bFGF. In a specific embodiment of the invention, the concentration of bFGF to be added to the media is between 1 and 1000 ng/ml. In a preferred embodiment of the invention, the concentration of bFGF in the media is between 10 and 100 ng/ml. In a more preferred embodiment of the invention, the concentration of bFGF in the media is between 20 and 50 ng/ml.

In an embodiment of the invention, the culture medium of the invention contains HGF. In a specific embodiment of the invention, the concentration of HGF to be added to the media is 10 to 1000 ng/ml. In a preferred embodiment of the invention, the concentration of HGF in the media is 50 to 750 ng/ml. In a more preferred embodiment of the invention, the concentration of HGF in the media is 100–500 ng/ml. In a specific embodiment of the invention, the Hu74 Medium of the invention contains HGF at a concentration of 100 ng/ml.

In addition, the present invention relates to Hu74 media comprising both HGF and bFGF. Addition of HGF to culture medium containing bFGF has been shown to have an additive stimulating effect on epidermal melanocytes in vitro.

The medium of the invention further comprises, one or more natural, non-toxic, physiological agents capable of promoting epidermal melanocytes proliferation in culture through cellular elevation of cAMP. As described herein, the use of epinephrine and α-MSH in cAMP deleted medium stimulated the growth, melanogenesis and migration of epidermal melanocytes.

In an embodiment of the invention, the concentration of αMSH in the media is between 1 and 1000 ng/ml. In a preferred embodiment of the invention, the concentration of αMSH is between 50 and 750 ng/ml. In a more preferred embodiment of the invention, the concentration of αMSH in the media is between 75 and 500 ng/ml. In a specific embodiment of the invention, Hu74 Medium contains αMSH at a concentration of 100 ng/ml.

In an embodiment of the invention, the concentration of epinephrine to be added to the media is between 1 and 3000 ng/ml. In a preferred embodiment of the invention, the concentration of epinephrine in the media is between 500 and 2000 ng/ml. In a more preferred embodiment of the invention, the concentration of epinephrine in the media is between 750 and 1750 ng/ml. In a specific embodiment of the invention, the concentration of epinephrine is 1.5 µg/ml. Because epinephrine is not very stable and is easily oxidized, antioxidants such as ascorbic acid (5 µg/ml) may be added to the Hu74 medium to stabilize the epinephrine.

In a specific non-limiting embodiment of the invention Hu74 Medium is prepared as follows. Glutamine is added to Ham's F12 (GIBCO, Carlsbad, Calif.) at a concentration of 2 mM. Gentamicin is added to the culture medium to obtain a final concentration of 50 µg/ml. Fetal bovine serum (FBS, GIBCO, Carlsbad, Calif.) is added to the medium to obtain a 10% concentration (volume/volume). The medium containing FBS and gentamicin is stored at 4° C. and prepared fresh every two weeks. bFGF (PeproTech, Rocky Hill, N.J.) is dissolved in F12 medium to 2,500 ng/ml and stored in small vials at –70° C. The stored solution is added to the culture medium to obtain a final concentration of 25 ng/ml once a week. HGF (PeproTech, Rocky Hill, N.J.) is dissolved in F12 medium to 10,000 ng/ml and stored in small vials at –70° C. The stored solution is added to the culture medium to obtain a final concentration of 100 ng/ml once a week. An α-MSH solution is obtained by dissolving the α-MSH powder (Sigma, St. Louis, Mo.) to 100 µg/ml and is stored at –70° C. The stored solution of α-MSH is added to the culture medium to obtain a final concentration of 100 ng/ml once a week. (L)-Epinephrine bitartrate (Sigma, St. Louis, Mo.) is dissolved in PBS at 0.15 mg/ml with sodium ascorbate (Sigma, St. Louis, Mo.) (0.5 mg/ml) and stored at –70° C. Ephinedrine and ascorbic acid are added to the culture medium to obtain a final concentration of 1.5 µg/ml of epinephrine and 5 µg/ml sodium ascorbate once a week.

Those of skill in the art will also recognize that one or more commercially available substances may be used as additives or substitutions to the medium to support the growth of epidermal melanocytes. Such growth may be monitored using a number of different methods. For example, proliferation of cells can be monitored by cell counts using a hemocytometer or flow cytometer; cell migration can be measured in chemotaxis assays using, for example, a Boyden chamber; and production of melanin can be measured using spectrophotometry.

5.2 Administration of Epidermal Melanocytes

In a specific embodiment of the invention, the cultured epidermal melanocytes of the invention are administered to a subject in need of skin pigmentation. Cultured epidermal melanocytes may be grafted directly onto the recipient where the cells will proliferate and migrate to form new skin tissue.

Prior to transplantation of cultured epidermal melanocytes, the epidermis of the depigmented or hypopigmented area of skin is removed down to the dermal-epidermal junction by superficial abrasion, which can be obtained by (i) mechanical methods, e.g., abraded at 25,000 revolutions per minute with a dermabrader fitted with diamond fraizes (Loentz et al., 1994, J Am Acad Dermatol 30:591–7), (ii) removal of the epidermis with a skin graft knife or laser, e.g., using a Silktouch Flashscanner attached to a Sharplan 1030 $CO_2$ laser at the setting of 4.5 to 7 watts with a 0.2 second pulse duration (Chen et al., 2000, J. Dermatol 27:434), (iii) application of YAG laser (Pai et al., 2002, J Eur Acad Dermatol Venereol 16:604), or (iv) by liquid nitrogen (Gauthier et al., 1992, J Am Acad Dermatol. 26:191).

The methods of the present invention may further be used in combination with human skin resurfacing techniques, including chemical peeling, dermabrasion, laser surgery, and various other methods for cosmetic purposes or scar removal. The methods utilize chemical, mechanical and laser techniques for removal of the upper dermal layers of the skin that can cause scarring and persistent redness. In an embodiment of the invention, epidermal melanocytes are applied to the skin after a skin resurfacing treatment.

The present methods and compositions may additionally employ cultured epidermal melanocytes genetically engineered to enable them to produce a wide range of functionally active biologically active proteins including, but not limited to, growth factors, cytokines, hormones, inhibitors of cytokines, peptide growth and differentiation factors, and extracellular matrix proteins. Methods which are well known to those skilled in the art can be used to construct expression vectors containing a nucleic acid encoding the protein of interest linked to appropriate transcriptional/translational control signals. See, for example, the techniques described in Sambrook, et al., 1992, Molecular Cloning, A Laboratory Manual, Cold Spring Harbor Laboratory, N.Y., and Ausebel et al., 1989, Current Protocols in Molecular Biology, Greene Publishing Associates & Wiley Interscience, N.Y.

In addition, cultured epidermal melanocytes may be attached in vitro to a natural or synthetic matrix that provides support for the transplanted epidermal melanocytes prior to, during, and/or post-transplantation. The matrix will have all the features commonly associated with being biocompatible, in that it is in a form that does not produce an adverse, or allergic reaction when administered to the recipient host. Growth factors capable of stimulating the growth and regeneration of, for example, skin tissue may also be incorporated into matrices. Such matrices may be formed from both natural or synthetic materials and may be designed to allow for sustained release of growth factors over prolonged periods of time. Thus, appropriate matrices will both provide growth factors and also act as an in situ scaffolding in which the epidermal melanocytes may proliferate and migrate. In preferred embodiments, it is contemplated that a biodegradable matrix that is capable of being reabsorbed into the body will likely be most useful.

To improve epidermal melanocytes adhesion to the matrix, survival, function and/or migration of the epidermal melanocytes, the matrix may optionally be coated on its external surface with factors known in the art to promote cell adhesion, growth, survival or migration. Such factors may include cell adhesion molecules, extracellular matrix molecules or growth factors.

Epidermal melanocytes can be administered to the recipient in an effective amount to achieve its intended purpose. More specifically, an effective amount means an amount sufficient to lead to the restoration of skin pigmentation or skin tissue function, thereby alleviating the symptoms associated with disorders resulting from genetic defects or tissue damage. The progress of the transplant recipient can be determined using visual inspection of the transplant area to assess cell coverage and skin pigmentation. The number of cells needed to achieve the purposes of the present invention will vary depending on the degree of tissue damage and the size of the affected skin area. Determination of effective amounts is well within the capability of those skilled in the art.

Cultured melanocytes can be detached from the culture flask by various enzymes, such as for example, by trypsin (0.05%,-EDTA (0.02%), at 37° C. for 3–10 minutes. The cell suspension is then centrifuged and the cells are resuspended with serum free Hu74 medium and placed in contact with the denuded area of the skin surface (Chen et al., 2000, J. Dermatol 27:434–439; Olsson et al., 1992, Lancet 340:981; Olsson et al, 1995, Br J Dermatol 132:587).

Alternatively, epidermal melanocytes can be administered to the recipient in one or more physiologically acceptable carriers. Carriers for these cells may include, but are not limited to, solutions of phosphate buffered saline (PBS), lactated Ringer's solution containing a mixture of salts in physiologic concentrations or culture medium with or without serum. In addition, the cells may be associated with a biocompatible matrix prior to administration into the recipient host.

The methods of the present invention encompass grafting of epidermal melanocytes onto the skin. The grafting of the epidermal melanocytes onto the desired region on the skin is accomplished by directly applying the cell layer to the area of the skin. In addition, growth factors or hormones may be administered to the recipient prior to and following transplantation for the purpose of priming the recipients tissue to accept the transplanted cells and/or to generate an environment supportive of cell proliferation and/or differentiation and/or migration and/or melanogenesis.

The site may be covered with a protective covering such as silicone (Chen et al., 2000, J. Dermatol 27:434) collagen dress (Olson et al., 1995, Br. J Dermatol 132:587–91) or fabric gauze. The gauze may be secured with Tegaderm (3M, St. Paul, Minn.) (Chen et al., 2000, J. Dermatol 27:434; Olsson et al., 1995, Br J. Dermatol 132:587). Patients are instructed to lie still for a period of time to allow the transplanted cells to adhere to the transplant site.

6. EXAMPLE

Culture of Epidermal Maelanocytes

These examples further describe and demonstrate embodiments within the scope of the present invention. The examples are given solely for the purpose of illustration and are not to be construed as limitations of the present invention, as many variations thereof are possible without departing from the spirit and scope of the invention.

6.1 Materials and Methods

6.1.1 Preparation of Medium

Glutamine was added to Ham's F12 (GIBCO, Carlsbad, Calif.) at a concentration of 2 mM. Gentamicin is added to the culture medium to obtain a final concentration of 50 $\mu$g/ml. Fetal bovine serum (FBS, GIBCO, Carlsbad, Calif.) is added to the medium to obtain a 10% concentration (volume/volume). The medium containing FBS and gentamicin is stored at 4° C. and prepared fresh every two weeks. bFGF (PeproTech, Rocky Hill, N.J.) is dissolved in F12 medium to 2,500 ng/ml and stored in small vials at −70° C. The stored solution is added to the culture medium to obtain a final concentration of 25 ng/ml once a week. HGF (PeproTech, Rocky Hill, N.J.) is dissolved in F12 medium to 10,000 ng/ml and stored in small vials at −70° C. The stored solution is added to the culture medium to obtain a final concentration of 100 ng/ml once a week. (L)-Epinephrine bitartrate (Sigma, St. Louis, Mo.) is dissolved in PBS at 0.15 mg/ml with sodium ascorbate (Sigma, St. Louis, Mo.) (0.5 mg/ml) and stored at −70° C. Epinephrine and ascorbic acid is added to the culture medium to obtain a final concentration of 1.5 $\mu$g/ml of epinephrine and 5 $\mu$g/ml sodium ascorbate.

Three deleted media were used for the study, (i) growth factor-deleted medium, (ii) cAMP-elevating agent deleted medium and (iii) serum-depleted medium. Various testing substances were added to the three deleted media above. These substances include bFGF, HGF, epinephrine and α-MSH. The deleted medium without the test substance was the negative control and the complete medium is the positive control.

Two culture media previously reported for culturing epidermal melanocytes used in transplantation of melanocytes (without TPA) were compared to Hu74 medium. The medium included that "Olsson's media" and "Hu16 media".

Olsson's medium is basal medium, supplemented with bFGF (5 ng/ml), dbcAMP (0.5 mM), glutamine (2 mM), penicillin (50 u/ml) and streptomycin (0.05 mg/ml).

Hu16 medium (FIC medium) is F12 medium, a commercially available basal medium, supplemented with bFGF (25 ng/ml), IBMX (0.1 mM), cholera toxin (10 ng/ml), glutamine (2 mM) and 10% FBS.

6.1.2. Isolation and Culture of Epidermal Melanocytes

Human skin specimens containing epidermis were obtained from a donor. The specimens were incubated in 0.25% trypsin solution (GIBCO, Carlsbad, Calif.) for 15 minutes at 37° C., followed by a 10 minute incubation with 0.2% EDTA (Sigma, St. Louis, Mo.) solution. The epidermal sheets were gently treated with forceps to dissociate the epidermal cells and to yield an epidermal cell suspension. The epidermal cells were centrifuged and seeded into a 25 cm$^2$ flask with the culture medium. The flask was incubated at 37° C. in an atmosphere of 95% humidified air and 5% $CO_2$. Geneticin (Sigma, St. Louis, Mo.) was added (100 μg/ml) for three days to eliminate keratinocytes and fibroblasts. The medium was changed every three days. The melanocytes typically reached confluence in two weeks. After reaching confluence, the melanocytes were detached using trypsin-EDTA solution, centrifuged, diluted and seeded for subculture. At the time of transplantation, the melanocytes were detached using trypsin-EDTA solution, centrifuged and resuspended with F12 medium.

6.1.4 Measurement of Cultured Epidermal Melanocyte Cell Growth

Cell counting was used to evaluate the effect of the test substance on growth of epidermal melanocytes. Epidermal melanocytes were plated in 6-well plates at a density of 1×10$^5$ cells per well with medium. After 24 hours, medium was replaced by the testing media. The media was changed every three days. After six days, the cells were detached with trypsin-EDTA solution and neutralized with culture medium with 10% serum. The cell suspension was centrifuged and the pellet was resuspended in 1 ml F12 medium, 20 μl of the cell suspension was collected into the tip of a Pasteur pipette and transferred to a hemocytometer. The hemocytometer was observed under an optical microscope. Cells falling in four 1 mm$^3$ areas bounded by three parallel lines were counted. The cell number was obtained using Formula I shown below (Freshney, 1987, Culture of Animal Cells. Wiley-Liss, Inc., New York, 2nd edition). The average of four counts was calculated. Triplicate samples were assayed in all experiments.

$$c = n \times 10^4 \qquad \text{FORMULA I}$$

where c=concentration (cells/ml), n=number of cells counted.

6.1.5 Melanin Production of Cultured Epidermal Melanocytes

Melanocytes cultured as described above were detached by trypsin-EDTA solution and counted in a hemocytometer. The cell suspensions were centrifuged and the pellet was resuspended in 1N NaOH. Melanin concentration was determined by measurement of optical density at 475 nm by a spectrophotometer and compared with a standard curve obtained using synthetic melanin (Sigma, St. Louis, Mo.). Melanin content is expressed as μg/culture or ng/cell (Hu et al., 1995, Invest. Ophthalmol Vis Sci 36:931).

6.1.6 Migratory Behavior of Cultured Epidermal Melanocytes

Cell migration experiments were performed on early passages of cells in 48-well Boyden chambers (Neuroprobe, Bethesda, Md.). Cultured epidermal melanocytes were dissociated with 0.05% trypsin-EDTA (Sigma, St. Louis, Mo.) at 37° C. for 2–3 minutes, neutralized by culture medium with 10% FBS. The cells were centrifuged and resuspended in culture medium. The lower half of the Boyden chambers contained culture medium with or without tested substances. An 8 μm pore cellulose nitrate filter separated the upper and lower wells. Epidermal melanocytes (3×10$^4$) suspended in 50 μl culture medium (with or without tested substances) were added to the upper wells. The chamber was incubated at 37° C. in a humidified atmosphere at 95% air and 5% $CO_2$. After 6 hours, the filter was removed from the chamber, fixed in 95% ethanol for 5 minutes, and stained with hematoxylin for 1 minute. The number of cells migrating through the filter and attached to the lower surface of the filter was counted (Doerr et al., 1996, J Biol Chem 271:2443; Verdoorn et al., 1986, Arch Ophtalmol 104:1216). Triplicate samples were assayed in all experiments.

6.1.7. Comparison of Long-term Effects on Cell Growth by Hu74 Medium with Other Culture Media The long-term results of epidermal melanocytes cultured with Hu74 medium, Hu16 medium and Olsson's medium were compared for three different cell lines. In each cell line, the epidermal melanocytes were seeded into three flasks at the first subculture, and cultured with 3 different media. Cells were incubated and subcultured continuously, until senescence. Population doubling (PD) of each generation was calculated from the number of cells plated and the number of cells harvested (Hu et al., 1992, Invest Ophthalmol Vis Sci 33:2443) using the following formula:

$$PD = (\log Nt - \log No)/\log 2 \qquad \text{Formula II}$$

No=cell number at the time of plating
Nt=cell number at the time of harvesting

The cumulative population doublings of a cell line cultured with a given culture medium is the sum of PD in all generations (Hu et al., 1992, Invest Ophthalmol Vis Sci 33:2443). The period of epidermal melanocytes cultured with each culture medium before senescence was also compared.

6.2. Results

6.2.1 Effects of bFGF on Cell Growth and Melanogenesis of Cultured Epidermal Melanocytes Epidermal melanocytes cultured in the absence of growth factor grew very slowly. Addition of bFGF at concentrations of 1–1,000 ng/ml caused a dose dependent stimulation of cell growth (FIG. 1A). Cell number of epidermal melanocytes cultured with bFGF was significantly greater than that of the controls (P<0.01 from 10–1000 ng/ml). However, bFGF did not show any significant influence on melanin content at any concentration (P<0.05) (FIG. 1B).

6.2.2 Effects of HGF on Cell Growth Melanogenesis and Migration of Cultured Epidermal Melanocytes Epidermal melanocytes cultured in the absence of growth factor grew very slow. Addition of HGF at concentrations of 1–1,000 ng/ml caused a dose dependent stimulation of cell growth (FIG. 2A). Cell number of epidermal melanocytes cultured with HGF was significantly greater than that of the controls (0.05>P>0.01 at concentration of 3 ng/ml and P<0.01 at 10–1000 ng/ml). HGF was also found to stimulate the production of melanin. Melanin content/well of epidermal melanocytes cultured with HGF was significantly greater than that of the controls (0.05>P>0.01 at concentration of 3 ng/ml and P<0.01 at 10–1000 ng/ml) (FIG. 2B).

In epidermal melanocytes cultured with 25 ng/ml of bFGF, addition of HGF (100 ng/ml) caused a further increase of cell growth and melanin content/well. The cell number of epidermal melanocytes cultured with HGF and bFGF was significantly greater than that cultured with bFGF alone (P<0.01). Melanin content/well in epidermal melanocytes cultured with HGF and bFGF was also significantly greater than cultured with bFGF alone. (0.05>P>0.01) (FIG. 2C).

Epidermal melanocytes cultured with HGF showed a better migratory behavior than that of the controls. Addition of HGF at concentrations of 1–1,000 ng/ml caused a dose dependent stimulation of migration (FIG. 2D). Migration cell number of epidermal melanocytes cultured with HGF was significantly greater that that of the controls (0.05>P>0.01 at a concentration of 10 ng/ml and P<0.01 at 10–1000 ng/ml).

6.3. Effects of Epinephrine on Cell Growth and Melanogenesis of Cultured Epidermal Melanocytes Epidermal melanocytes cultured without cAMP-elevating agents grew very slowly and showed a relatively low melanin content/well. Addition of epinephrine at concentrations from 1–3,000 ng/ml caused a dose dependent stimulation of cell growth (FIG. 3A). Cell number of epidermal melanocytes cultured with epinephrine was significantly greater than that of the controls (0.05>P>0.01 at concentration of 3 ng/ml and P<0.01 at 10–3000 ng/ml). Epinephrine also stimulated the production of melanin. Melanin content/well of epidermal melanocytes cultured with epinephrine was significantly greater than that of the controls (0.05>P>0.01 at concentration of 3 ng/ml and P<0.01 at 10–3000 ng/ml) (FIG. 3B).

6.2.4. Effects of α-MSH on Cell Growth and Melaongenesis of Cultured Epidermal Melanocytes Epidermal melanocytes cultured with cAMP elevating agents grew very slowly and showed a relatively low melanin content/well. Addition of α-MSH at concentrations from 1–1,000 ng/ml caused a dose dependent stimulation of cell growth (FIG. 4A). Cell number of epidermal melanocytes cultured with α-MSH was significantly greater than that of the controls (0.05>P>0.01 at concentration of 1 ng/ml and P<0.01 at 10–1000 ng/ml). α-MSH also stimulated the production of melanin. Melanin content/well of epidermal melanocytes cultured with α-MSH was significantly greater than that of the controls (0.05>P>0.01 at concentration of 1 ng/ml and P<0.01 at 10–1000 ng/ml) (FIG. 4B).

6.2.5. Comparison of Hu74 Medium to Other Culture Media

Epidermal melanocytes cultured with Hu74 medium grew better than cells cultured in Hu16 medium and Olsson's medium. Cell number of epidermal melanocytes cultured with Hu74 medium was significantly greater than that cultured in Hu16 medium and Olsson's medium (0.05>P>0.01, Hu74 medium compared with Hu16 medium and P<0.01, Hu74 medium compared with Olsson's medium) (FIG. 6).

6.2.6 Comparison of Long-term Growth Effects of Hu74 Medium with Other Culture Media Three cell lines of epidermal melanocytes were cultured with Hu74 medium, Hu16 medium and Olsson's medium from the first subculture and passaged until senescence. Epidermal melanocytes cultured with Hu74 medium could be passaged for 111.7±4.5 days before senescence, which was significantly longer than that cultured with Hu16 medium (86.7±6.5 days, 0.05>P>0.01), and was very significantly longer than that of Olsson's medium (32.3±9.5 days, P>0.01) (FIG. 7). Epidermal melanocytes cultured with Hu74 medium divided 30.4±1.91 times (cumulative population doubling), which was very significantly more than that cultured with Hu16 medium (22.9±1.34) and Olsson's medium (4.3±0.35) (P>0.01 in Hu74 medium as compared with both Hu16 or Olsson's media) (FIG. 7).

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are incorporated by reference in their entireties.

We claim:

1. A composition for culturing epidermal melanocytes comprising basal medium, serum, one or more antibiotics, one or more growth factors, and one or more natural, physiological cAMP-elevating agents, wherein the one or more natural, physiological cAMP-elevating agents comprises epinephrine, and wherein the one or more growth factors comprises hepatocyte growth factor.

2. The composition of claim 1, wherein the serum is selected from the group consisting of bovine serum, newborn bovine serum and fetal bovine serum.

3. The composition of claim 2, wherein the serum is fetal bovine serum.

4. The composition of claim 1, wherein the basal medium is selected from the group consisting of Ham's F12, RPMI and DMEM.

5. The composition of claim 4, wherein the basal medium is Ham's F12.

6. The composition of claim 1, wherein the one or more growth factors further comprises a growth factor selected from the group consisting of basic fibroblast growth factor, epidermal growth factor, transforming growth factor-β, and a combination thereof.

7. The composition of claim 6, wherein the one or more growth factors is a combination of hepatocyte growth factor and basic fibroblast growth factor.

8. The composition of claim 1, wherein the one or more natural, physiological cAMP-elevating agents further comprises α-melanocyte stimulating factor.

9. The composition of claim 8, wherein the one or more natural, physiological cAMP-elevating agents is a combination of epinephrine and α-melanocyte stimulating factor.

10. A method of obtaining epidermal melanocytes comprising:
   isolating epidermal melanocytes from a donor; and
   culturing the epidermal melanocytes using the composition of claim 1, wherein the cultured epidermal melanocytes exhibit proliferative growth, melanin production and migratory behavior.

11. The method of claim 10, wherein the epidermal melanocytes are isolated from a skin sample.

12. The method of claim 11, wherein the skin sample is obtained from a minigraft or a blister top.

13. The method of claim 12, wherein the skin sample is obtained from a blister top.

14. The method of claim 13, wherein the blister top is removed from a suction blister obtained by applying a vacuum to the surface of the skin.

15. The method of claim 11, wherein the skin sample is treated mechanically and/or enzymatically to dissociate epidermal melanocytes from other cells and tissues in the skin sample.

16. The method of claim 15, further comprising incubating the skin sample in geneticin wherein the incubation inhibits the growth of keratinocytes and fibroblasts.

17. A method of providing a subject in need of skin pigmentation with a proliferating population of epidermal melanocytes comprising
    isolating epidermal melanocytes from said subject;
    culturing the epidermal melanocytes using the composition of claim 1; and
    applying the cultured epidermal melanocytes to the skin of said subject,
    wherein the cultured epidermal melanocytes exhibit proliferative growth, melanin production and migratory behavior.

* * * * *